United States Patent [19]
Dimoudis et al.

[11] Patent Number: 5,980,888
[45] Date of Patent: Nov. 9, 1999

[54] KERATINOCYTES ATTACHED TO MICROCARRIERS FOR TREATMENT OF SKIN WOUNDS

[75] Inventors: Nikolaos Dimoudis, Wielenbach; Anton Hartinger, München, both of Germany

[73] Assignee: Roche Diagnostics GmbH, Mannheim, Germany

[21] Appl. No.: 08/809,408

[22] PCT Filed: Oct. 24, 1995

[86] PCT No.: PCT/EP95/04164

§ 371 Date: Apr. 23, 1997

§ 102(e) Date: Apr. 23, 1997

[87] PCT Pub. No.: WO96/12510

PCT Pub. Date: May 2, 1996

[30] Foreign Application Priority Data

Oct. 25, 1994 [DE] Germany ............... 44 38 015

[51] Int. Cl.⁶ .............. C12N 5/00; C12N 11/02; C12N 11/10; C12N 5/06
[52] U.S. Cl. ............ 424/93.7; 424/422; 424/499; 435/176; 435/177; 435/178; 435/395; 435/403
[58] Field of Search ................. 435/366, 395, 435/402, 403, 404, 405, 176, 177, 178; 424/93.7, 422, 499

[56] References Cited

U.S. PATENT DOCUMENTS

| | | | |
|---|---|---|---|
| 4,016,036 | 4/1977 | Green | 435/347 |
| 4,940,666 | 7/1990 | Boyce et al. | 435/240.2 |
| 5,709,854 | 1/1998 | Griffith-Cima et al. | 424/93.7 |
| 5,712,163 | 1/1998 | Parenteau et al. | 435/405 |

FOREIGN PATENT DOCUMENTS

| | | |
|---|---|---|
| 1 215 922 | 12/1986 | Canada . |
| 0 242 270 | 10/1987 | European Pat. Off. . |
| 0 242 305 | 10/1987 | European Pat. Off. . |
| 0 267 015 | 5/1988 | European Pat. Off. . |
| 0 333 328 | 9/1989 | European Pat. Off. . |
| 0 361 957 | 4/1990 | European Pat. Off. . |
| 0 489 332 | 6/1992 | European Pat. Off. . |
| 2 059 991 | 4/1981 | United Kingdom . |

OTHER PUBLICATIONS

International Publication No. WO 81/00260 published Feb. 5, 1981.
International Publication No. WO 89/03228 published Apr. 20, 1989.
International Publication No. WO 89/03392 published Apr. 20, 1989.
International Publication No. WO. 89/08467 published Sep. 21, 1989.
International Publication No. WO 90/02796 published Mar. 22, 1990.
International Publication No. WO 90/13625 published Nov. 15, 1990.
International Publication No. WO 92/06179 published Apr. 16, 1992.
International Publication No. WO 93/10217 published May 27, 1993.
International Publication No. WO 93/23088 published Nov. 25, 1993.
Altankov et al., *J. Biomater. Sci. Polymer Edn*, vol. 2, No. 2, 1991, pp. 81–89. "Synthesis of protein–coated gelatin microspheres and their use . . .".
Boyce et al., *Surgery*, vol. 103, No. 4, (Apr.) 1988, "Biologic attachment, growth, and differentiation of cultured human epidermal keratinocytes . . .".
Database WPI, Section Ch, Week 9436, Derwent Publications Ltd., London; Class B04, AN 94–292256, 1994.
Database WPIL, Week 9244, Derwent Publications Ltd., London, GB; AN 92–360004, 1992.
Lausanne International Congress on Burns, Jun. 25–28, 1991, Lausanne, Switzerland; The International Society for Burn Injuries; Abstract: N. Serdev et al., "Keratinocytes adhered on collagen microcarriers for burn treatment".
The Jerusalem International Meeting on Burn Injuries, Jerusalem, Israel, Jun. 9–12, 1992; Abstract: N. Serdev et al. "Artificial skin formation in vivo using a composite keratinocyte/collagen graft. 1. Hystological findings and clinical cases".
Tinois et al., *Arch. Dermatol. Res.*, 279, 1987, pp. 241–246, "Growth and differentiation of human keratinocytes on extracellular matrix".

(List continued on next page.)

*Primary Examiner*—David M. Naff
*Attorney, Agent, or Firm*—Nikaido Marmelstein Murray & Oram, LLP

[57] ABSTRACT

Epithelial cells are attached to microcarriers to form a transplantation material for treatment of skin wounds. Preferably, keratinocyte-covered microcarriers are prepared using microcarriers having a diameter of 50 to 500 $\mu$m, and obtaining a coverage of keratinocytes of 30 to 100% of the maximum coverage. An optimum coverage is between 50 and 80% and preferably between 60 and 70%. Keratinocytes are selected from autologous cells, allogenic cells and a combination of these cells. The microcarriers may be pre-coated with eukaryotic cells or an extracellular matrix protein such as collagen before keratinocytes are attached. The keratinocyte-covered microcarriers may be combined with a cryoprotective substance for storage at +3° C. to –196° C. prior to use. Keratinocytes are attached to the microcarriers by pre-culturing the keratinocytes, and then culturing the keratinocytes in the presence of the microcarriers while intermittently stirring. A serum free culture medium may be used. Initial culturing in the presence of the microcarriers may be in the smallest amount of medium required to prevent the keratinocytes from dying, and after keratinocyte attachment, adding medium to provide a volume for optimum growth. The keratinocyte-covered microcarriers are applied to a skin wound and the wound is covered with a protective dressing. A pharmaceutical formulation and kit are prepared containing the keratinocyte-covered microcarriers may.

36 Claims, 3 Drawing Sheets

OTHER PUBLICATIONS

Tinois et al., *Experimental Cell Research,* 193, 1991, pp. 310–319, "In Vitro and Post–transplantation Differentiation of Human Keratinocytes . . .".

Wilke and Furcht, *The Journal of Investigative Dermatology,* vol. 95, No.3 (Sep.) 1990, pp. 264–270, "Human Keratinocytes Adhere to a Unique Heparin–Binding Peptide Sequence Within the Triple Helical Region of Type IV Collagen".

Williams et al., *Journal of Cellular Physiology,* 136, 1988, pp. 103–110, "Lipid Content and Metabolism of Human Keratinocyte Cultures Grown at the Air–Medium Interface".

KERATINOCYTES ATTACHED TO MICROCARRIERS FOR TREATMENT OF SKIN WOUNDS

This application is a 371 of PCT/EP95/04164, filed Oct. 24, 1995.

BACKGROUND OF THE INVENTION

1. Field of the Invention

The subject-matter of the invention is a new biomaterial which contains epithelial cells on microcarriers (MCs), as well as the preparation and use of said biomaterial for preparing a medicament.

2. Description of the Prior Art

Skin consists of the epidermis, the basement membrane and the dermis. The epidermis forms the outer coat. The dermis consists essentially of fibroblasts with additional substances such as, e.g., collagen. The basement membrane essentially contains keratinocytes which are non-differentiated but proliferating. The epidermis essentially contains differentiated keratinocytes wherein the upper layer is horny. It is true that while the degree of differentiation of the cells is increasing, the ability of the cells to proliferate is decreasing. Accordingly, the non-differentiated keratinocytes exhibit the highest proliferation potency.

Burn wounds and slow-healing wounds (ulcers) usually are treated with skin sheets consisting of autologous keratinocytes (classical method). To this end, a piece of skin is cut off from the patient, the keratinocytes are cultured in vitro, and the expanded skin sheets so obtained are transplanted [Gallico, G. G., et al., New Engl. J. Med. 311 (1984) 448–451 (1); Cuono, C., et al., Lancet (1986) 1123–1124 (2); De Luca, M., et al., Burns 15 (5) (1989) 303–309 (3); Gallico, G. G., Clinics in Plastic Surgery 17 (3) (1990) 519–526 (4); De Luca, M., and Cancedda, R., Burns 18 (1) (1992) 5–9 (5)]. The transfer of thin skin sheets from cell culture flasks to, e.g., Vaseline gauze as well as the fixing thereof onto the wound surface is problematical. The covering of wounds on parts of the body that are difficult to reach is another problem. Besides this, only keratinocytes can be transferred by means of such classical skin sheets. Skin sheets from keratinocytes involve the drawback that these cells are almost completely differentiated when the sheets are being formed, which means that the sheets practically no longer contain any keratinocytes capable of proliferation. Thus, these sheets constitute a transplantation material which cannot grow, or continue growing, after transplantation. Epidermal transplants (classical skin sheets) with allogenic keratinocytes have been carried out in a number of clinics without any immunological rejection reactions being observed (Gboyse, S. T., et al., Plast. Reconst. Surg. 91 (1993) 632 (17); Burt, A. M., et al., Br. Med. J. 298 (1989) 915 (18); Hickerson, W. L., et al., Burns 20/1 (1994) 52 (19)).

From WO 92/06179 (6) and EP-A 0 242 270 (7) biomaterials are known which contain epithelial cells within a collagen gel. In this context, epithelial cells (fibroblasts or keratinocytes) are embedded in gel layers. It is known that such gels may also contain keratinocytes. However, the keratinocytes in the gel are immobilized and are thus incapable of proliferating and differentiating to an appreciable extend after transplantation. Accordingly, keratinocytes from such gels are not able to form a basement membrane and an epidermis. Another drawback of this biomaterial is, in particular, the low rate of migration of the epithelial cells from the biomaterial into the wound. Furthermore, the handling and fixing of these biomaterials is very difficult and laborious.

In WO 90/02796 (8) there is described a three-dimensional cell culture system on the basis of, for instance, cellulose, polyamide, polyester, on which epithelial cells can grow. In this context, an artificial tissue is obtained which is covered with epithelial cells (fibroblasts or keratinocytes) and which is said to be suitable for transplantation. These artificial transplantation materials, too, do not exhibit any advantage over the skin sheets applied in the classical method.

SUMMARY OF THE INVENTION

The object of the invention is to provide a biomaterial which does not exhibit the drawbacks described and which can be prepared in an easy manner and in large quantities. The subject-matter of the invention is the use of a biomaterial which contains epithelial cells adherently attached to microcarriers, for preparing a transplantation material for the treatment of skin wounds. The present invention makes it possible to:

1. transfer non-differentiated and, thus, potent keratinocytes that are capable of proliferation;
2. form a basement membrane and an epidermis on the wound after transplantation (the non-differentiated keratinocytes, after transplantation, separate from the microcarriers and proliferate and differentiate).

It was heretofore unknown that non-differentiated keratinocytes which are capable of proliferation, can be cultured in vitro. The method according to the present invention, makes it possible to produce such keratinocytes. Thus, the present method is susceptible of industrial application directly in vitro. Non-differentiated keratinocytes produce components which are different from those produced by differentiated keratinocytes (which, according to the prior art, have heretofore been the only ones obtained by culturing in vitro). An example of such a component is collagen IV. Accordingly, the invention offers a method of producing substances, such as collagen IV, by culturing non-differentiated keratinocytes. The non-differentiated keratinocytes can be selected by using immune staining with the markers Ki67, keratin 10 and keratin 14 (Slivka, S. R., et al., J. Invest. Dermatol. 100 (1993) 4046 (15); Regnier, M., et al., Skin Pharmacol. 3 (1990) 70–85 (16)).

DETAILED DESCRIPTION OF THE INVENTION

As epithelial cells, all epithelial cells, such as, for instance, keratinocytes, fibroblasts and endothelial cells, are suitable. Such cells preferably are proliferating cells, and most preferably, non-confluent cells which have the properties of basal cells. CellGenesys is engineering epidermal keratinocytes to have "universal properties" so that they can be used in a full thickness skin (epidermis and dermis) graft without causing a donor-host immune response. (CellGenesys, research collaboration with Advanced Tissue Sciences, SCRIP No. 1961, 27 September 1994, p. 24).

By "microcarriers" there are to be understood small solid particles which are capable of being suspended in a slowly stirred, aqueous medium. Such microcarriers are used for the cultivation of eukaryotic cells, wherein the cells grow on the surface of these particles, in the form of a confluent layer. Microcarriers of this kind and their application in cell cultures are described, for instance, in Advances in Applied Microbiology 31 (1986) 139–179.

As microcarriers there may be used all microcarriers which consist of a biocompatible material (such as, e.g., collagen, polymers from hyaluronic acid or hyaluronane esters (e.g. ethyl or benzyl esters) (Andreassi, L., et al., Wounds 3 (1991) 116–126 (28); Myers, S. R., et al., Abstract No. 85 in 5th Annual Meeting of the European Tissue Repair Society (August 1995), Padua (29)) (e.g. HYAFF-11™ from FIDIA Advanced Biopolymers, Abano T., Italy), fibrin binding polypeptides, dextran, gelatin, silicone, etc.) or of a suitable mixture of several biocompatible materials. There may be used, for example, Cytodex3® (crosslinked dextran matrix with a denatured collagen layer, 100–230 µm) (Pharmacia AB, Sweden) based on dextran Cellgen (Koken Co., Japan), a reconstituted and crosslinked collagen from bovine skin, 200–500 µm, or Cultispher-G® (macroporous gelatin microcarrier) (Hyclone, Greiner, Germany) based on gelatin.

The size of the microcarriers is not critical. Usually, however, the carriers have a diameter of 50 to 500 µm. Microcarriers of a diameter below 50 µm are so small that they usually cannot be sufficiently covered with cells growing on them. Microcarriers of a size higher than 500 µm are so large that, on the one hand, a high coverage with cells is difficult to achieve; and on the other hand, these particles are not optimal with regard to transplantations because the detachment of the epithelial cells and spreading on the wound does not proceed satisfactorily in the case of such particles.

Surprisingly, it has been found that for an epidermal graft according to the invention there need not be used autologous cells as are applied in the known methods, but rather allogenic cells alone or mixtures of autologous and allogenic cells are also suitable. This offers the advantage that it is not necessary to prepare for each patient, in a time-consuming cultivation, a completely autologous transplantation material. The allogenic transplantation material can be standardized and will be available then in large amounts and at any time. This is especially important in the case of use for the treatment of large-area burns which must be treated as quickly as possible.

Allogenic keratinocytes, after transplantation, are essentially not rejected. However, it is not these keratinocytes themselves which form the new skin. The essential function of the non-differentiated allogenic keratinocytes is to stimulate those keratinocytes of the transplant recipient which are still present (these non-differentiated keratinocytes will form other components than those formed by differentiated keratinocytes). They secrete a large number of hormones (vitamin D, steroids, and others), cytokines (interleukin 1, 3, 6, PDGF, bFGF, TGF-α, TGF-β, and others) as well as matrix elements (laminine, type IV/-VII collagen, fibronectin), which effect an accelerated epithelization extending from the margin of the wound as well as of remaining areas of cutaneous appendage (which still contain residues of intact keratinocytes) (Brown, H., "Wound healing research through the ages", wound healing: biochemical and clinical aspects, Saunders, Philadelphia, page 5, editors: Cohen, I. K. Diegelman R. F., and Lindblad, W. J., 1992 (14)). In burns of the IIb degree, for instance, where residues of the patient's own keratinocytes are still present, using an allogenic transplant or a mixed transplant comprising allogenic and autologous keratinocytes, will be sufficient. The allogenic keratinocytes stimulate the remaining keratinocytes of the recipient and themselves die off after some time. In high degree buns (third degree), practically no keratinocytes will be present any longer. In such cases, a transplantation of autologous keratinocytes is necessary.

The time until the start of treatment can be considerably shortened also by using a biomaterial containing a reduced portion of autologous cells. In a preferred embodiment, the biomaterial may contain 10 to 30% of autologous cells. As far as the remainder of 70 to 90% is concerned, one may resort to stored allogenic biomaterial available in large amounts. By this the time for preparing a sufficient amount of transplantation material can be shortened because only a small amount of autologous cells of the cultivation need be obtained.

In addition to this, the biomaterial according to the invention offers new possibilities of preparing individual transplantation materials. For example, it is possible to prepare the transplantation material immediately before transplantation. This can also be done by mixing biomaterial according to the invention containing autologous and/or allogenic epithelial cells and/or various epithelial cells (e.g. keratinocytes or fibroblasts). By this the specific requirements of the wound to be treated (e.g. degree of burn, burn wound or type of wound) can be taken into account optimally.

This individual adaptation of the composition of the biomaterial to the transplantation problem is impossible to achieve with the prior art transplantation materials.

In order to prepare the biomaterial, the autologous and/or allogenic epithelial cells are isolated, in a manner known to one skilled in the art [Rheinwald, J. G., and Green, H., Cell 6 (1975) 331–334 (9); Limat, A., et al., J. Invest. Dermatol. 92 (1989) 758–762 (10)], from human or animal material and, suitably, are first pre-cultured adherently. Preferably after the first or the second passage, the cells are cultured further together with the microcarriers. This is accomplished either in a stirred culture (spinner culture or fermenter) or in a quiescent culture (e.g. cell culture flasks), wherein the cells spread out from the bottom of the cell culture flasks onto the microcarriers. It is also preferred to incubate beads, which have been allowed to swell in water, with the cells over a period of 2 to 5 hours, preferably 3 to 4 hours, and while doing so, to stir the culture briefly (for 3 to 5 minutes) once an hour.

In a preferred embodiment, the microcarriers can be pre-coated in order to improve the adhesion of the cells and enhance the extent of coverage of the microcarriers. For the coating, for instance proteins of the extracellular matrix, such as fibronectin or collagen, or whole eukaryotic cells (e.g. fibroblasts incapable of proliferation) or components thereof (e.g. membrane fractions) may be used.

Preferably, prior to cultivation, the microcarriers are coated with epithelial cells incapable of proliferation, such as, e.g., fibroblasts. Suitable fibroblasts are, for example, killed mouse fibroblasts from the cell line 3T3. Such a pre-coating according to the methods known to one skilled in the art is described in DE 26 51 685, for instance. It is also preferred to pre-coat the microcarriers with substances which improve the adhesion of the cells (e.g. collagen). Suitably, the pre-coating is carried out after swelling of the microcarriers and autoclaving for sterilization, but before incubation with the epithelial cells. To this end, the microcarriers are incubated with an aqueous solution of such an adhesion molecule or the cell suspension (the latter, suitably, in cell culture medium). Thereafter, the coated microcarriers are washed [preferably with PBS (phosphate buffered saline) NaCl: 8000 mg/l, KCl: 200 mg/l, Na$_2$HPO$_2$H$_2$O:1440 mg/l, KH$_2$PO$_4$:200 mg/l].

In order to coat the microcarriers with the epithelial cells, preferably the cultivation is carried out in serum-free medium, optionally with pituitary extract (bovine) or fetal calf serum being added.

In a preferred embodiment, growth- and cell differentiation-promoting factors, respectively, such as keratinocyte growth factor (KGF), nerve growth factor (NGF) or platelet-derived growth factor (PDGF), are added in order to enhance the extent of coverage.

After the desired extent of coverage has been attained, the cells are isolated. This can be accomplished, for instance, by sedimentation or centrifugation at low g-values (e.g. 10 to 50 g).

The cells isolated in this manner either are applied directly in a suitable galenic formulation for treatment of wounds or are preserved until treatment. For preservation, ordinarily cryopreservation is suitable. Cryopreservation is carried out preferably with the addition of cryoprotective substances, such as dimethyl sulfoxide (DMSO) or glycerol, at a temperature of +3° C. to −196° C., preferably for long-term storage (more than 6 hours). In the case of short-term storage (less than 6 hours), preservation can be carried out at a temperature of +3° C. to +10° C. without the addition of cryoprotective substances.

In order to prepare a biomaterial containing autologous and allogenic cells attached to microcarriers, preferably autologous epidermal cells are first isolated and cultured in the presence of the microcarriers. The cultivation is carried out for a sufficient time until the amount of autologous biomaterial desired as a proportion in the mixture has been attained. Then, allogenic biomaterial (which contains allogenic epithelial cells adherently attached to the microcarriers) is added and the epidermal graft according to the invention is prepared, as a mixture. In this context, it is preferred to employ cryopreserved allogenic biomaterial or allogenic biomaterial that has been stored at a temperature between +3° C. and +10° C.

Preferably, the proportion of autologous biomaterial in the mixture is between 10 and 30%. It is also possible to culture autologous and allogenic cells together in the presence of microcarriers. In such case, one will obtain a transplantation material in which both autologous and allogenic cells are attached to the individual microcarriers.

In a further preferred embodiment, a mixture is used which consists of microcarriers wherein each individual microcarrier particle is covered with one type of epithelial cells only, such as, e.g., fibroblasts or keratinocytes. It is also possible to use microcarriers on which several types of epithelial cells (preferably, fibroblasts and keratinocytes (fetal or adult)) are adherently attached. The ratio of mixing of the differently covered microcarriers or the ratio of mixing of the individual cells on one microcarrier may actually be any ratio desired and may vary depending on the intended use (e.g. burn wounds, senile ulcers, diabetic ulcers). In this context it is preferred to apply, for diabetic wounds, only fibroblasts, or fibroblasts in excess, and for burn wounds, only keratinocytes, or keratinocytes in excess over the other epithelial cells in the transplantation material.

The extent of coverage of the microcarriers with epithelial cells can be varied widely. However, the lower the coverage, the lower the efficacy of the transplant. Hence, in practice, it is advantageous to apply a coverage as high as possible.

The preferred coverage is between 30 and 100%. Surprisingly, it has been found, however, that a coverage between 50 and 80%, preferably between 60 and 70%, is optimum.

By coverage there is to be understood the average amount of cells adherently attached to the microcarrier, in reference to complete coverage.

Figure 1:
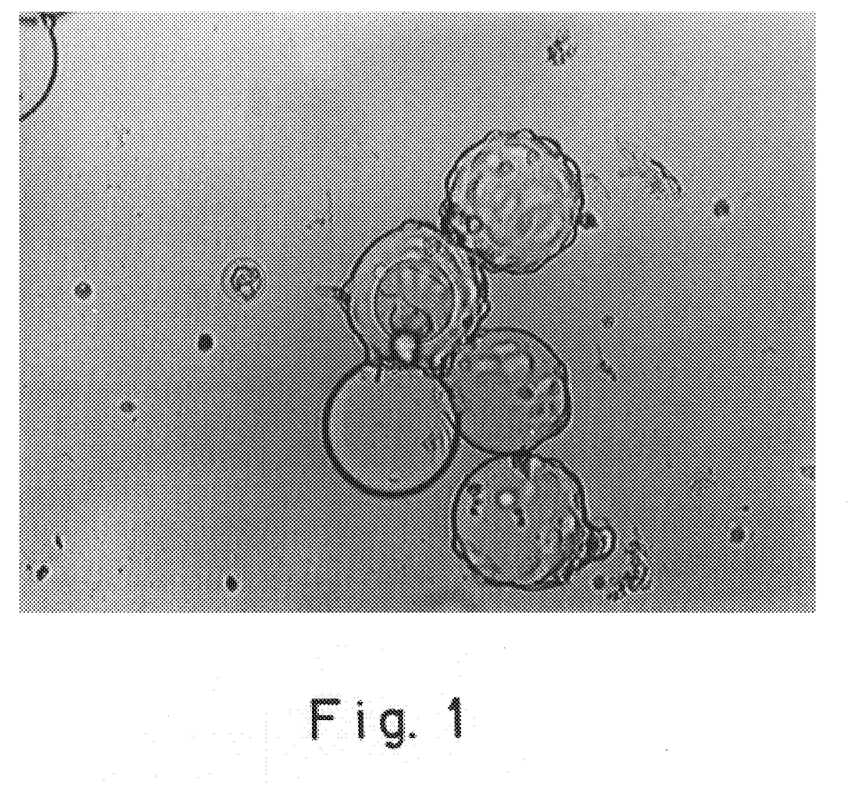
FIG. 1 shows Cytodex 3® (crosslinked dextran matrix with a denatured collagen layer) microcarriers with a 30% coverage with keratinocytes (example 2).
Figure 2:
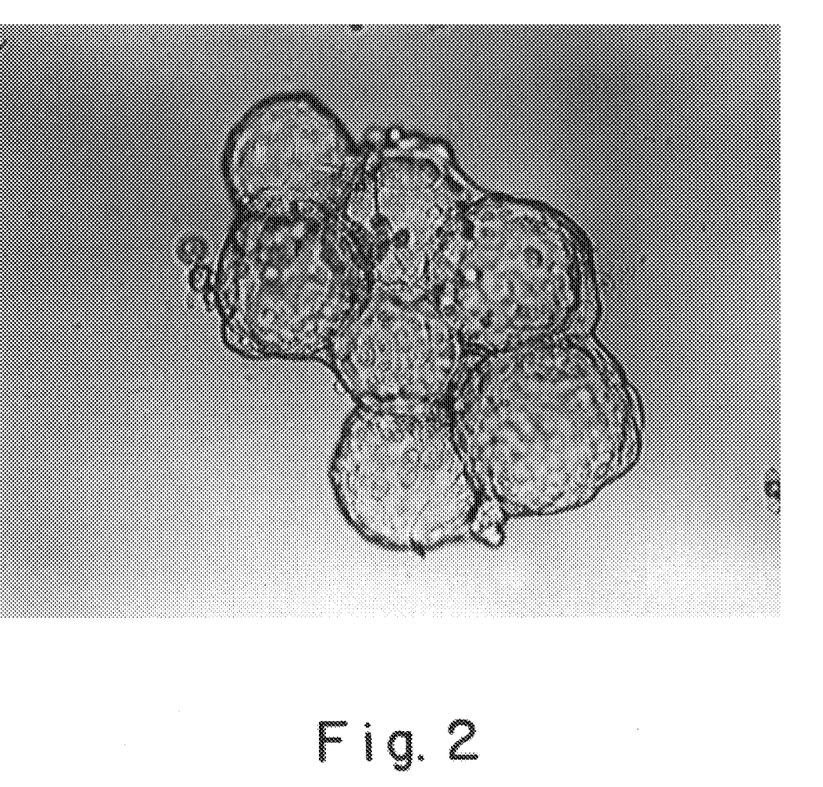
FIG. 2 shows the same system with 80% coverage.

This amount can be determined either visually under the microscope or after detachment of the cells from the microcarriers (for instance, by treatment with trypsin) and staining. Suitably, the complete coverage can be determined most easily visually under the microscope. Typical pictures of a 30% and 80% coverage of the microcarriers according to the invention are shown in FIGS. 1 and 2.

For therapeutic application, the preserved biomaterial (optionally mixed with fresh biomaterial which may also be autologous) is used.

To this end, the biomaterial is thawed, optionally the cryoprotective substance is removed by washing with medium, and the biomaterial is mixed with a preparation which constitutes the galenic medium. It is essential for the galenic formulation that the material used should not dehydrate the cells. It has been found that hydrogels, preferably based on methyl cellulose, are particularly suitable for this purpose. Examples of suitable hydrogels are as follows:

methyl cellulose (preferably about 4%, non-ionogenic cellulose derivatives, i.e., modified D-glucoglycans in which the hydroxyl groups of the cellulose are substituted with methyl groups) (Keresztes, A., Kedvessy, G., Pharmacia 20 (1965) 371 (20); Sarkar, N., J. Appl. Polymer Sci. 24 (1979) 1073) (21);

alginates (salts of alginic acid, e.g., sodium-, calcium-, magnesium- or ammonium alginate, e.g., Kelco-Alginates® of the firm of Kelco) (Sellerie, R., et al., Boll. chim. farmaceut. Milano 119 (1980) 41 (22); Daigo, K., et al., Yakuri to Chiryo 11 (1983) 401) (23);

agarose (polysaccharide from agarobiose and neo-agarobiose) (Langford, J. J., Dambach, A. E., Soap. Chem. Specialties 45/5 (1969) 231) (24).

Type I collagen and type m collagen in medium may also be suitable.

It is also possible to use methyl cellulose dissolved in culture medium. The viscosity must be such that the material is easy to spread and that the cells can separate after transplantation and are capable of migration in order to form, e.g., as keratinocytes a basement membrane and an epidermis.

The basis of the galenic medium suitably is essentially the culture medium. It is, however, advantageous to add further substances which are compatible with the skin and with which the viscosity of the biomaterial can be altered. Optimizing the viscosity is especially advantageous for optimizing the handling of the biomaterial in applying it to the wounds, and for adhesion to the wounds. Suitable skin-compatible substances for altering the degree of viscosity are, for instance, thickening agents, auxiliary emulsifying agents, hydrocolloids or gelling agents, such as, e.g., gelatin, pectin, alginates, cellulose derivatives, Aqualose and polysaccharides.

Suitably, these substances are admixed to the galenic medium at such concentration that the microcarrier preparation is easy to apply.

In a preferred embodiment, the galenic medium may further contain substances that additionally improve wound healing, such as, e.g., NGF, TGF-β, PDGF, KGF and/or fibronectin or analogs (Schärffetter-Kochanek, K., et al., J.

Invest. Dermatol. 98 (1992) 3–11 (30); Lange, T. S., et al., J. Exp. Dermatol. 4 (1995) 130–137 (31); WO 92/09200 (32) (for fibronectin peptides); WO 90/07577 (33); WO 91/17765 (36)), which improve the adhesion of the epithelial cells on the wound bed, especially after the cells have become detached from the carrier. Preferably, the medicament contains between 0.03 g and 0.1 g of fibronectin or analogs per gram of galenic medium. It is further preferred that the galenic medium should contain viable cells having the properties of macrophages, e.g., macrophages or Langerhans' cells for disinfecting the wounds. It is preferred that the medicament should contain about 10 to 30% of such cells.

The medicament according to the invention, as an epidermal graft, is suitable for use in the treatment of, for instance, burn wounds, diabetic wounds, senile ulcers and other slow-healing wounds. The medicament according to the invention is also suitable for speeding up the healing of normal wounds. A further use is in plastic surgery.

An essential advantage of the biomaterial according to the invention lies in the fact that, unlike the known epidermal grafts, it is flexible in all directions and easy to adapt to the body surface even on parts which are problematical (e.g. skinfolds, ear, eyelids).

For application, suitably, the medicament according to the invention is placed on the wounds using an appropriate dressing depending on the type of wound to be treated [for example: a) fatty gauze dressing, e.g., GRASSOLIN® of the firm of Hartmann, Germany, b) hydrophobic polymer dressing, e.g., EPI-LOCK® of the firm of Merck & Co., Missouri/USA, c) hydroactive dressing, e.g., DUODERM® [gel formula dressing] of the firm of Conva Tec, Princeton/USA d) MITRAFLEX (microporous polyurethane membrane)], in order to maintain its effectiveness.

In a preferred embodiment, a mixture of autologous and allogenic epithelial cells, in particular keratinocytes, is used.

As keratinocytes, preferably epidermal keratinocytes (e.g. foreskin keratinocytes) are used.

In order to prepare a biomaterial based, in particular, on keratinocytes it is specifically preferred to pre-coat the microcarriers, as described above. Intermittent stirring is also preferred in the culturing of the cells in the presence of the microcarriers. To this end, the culture is preferably stirred for a few minutes (e.g. 1 to 5 minutes) at a speed between 10 and 100 rpm and subsequently cultured further for an extended period of time (about 20 to 40 minutes), without stirring. The intermittent stirring conditions are maintained over the entire period of culturing. It has been found that it is specifically advantageous for the culturing if stirring is carried out for about 2 minutes at about 40 rpm, followed by a rest period of about 30 minutes. These conditions may, of course, be varied to a certain extent. In this context care must be taken that stirring is carried out for a period as short as possible, yet attaining a thorough mixing of the medium, so that subsequently, culturing can be carried out as long as possible without stirring and with the cell growth and the adhesion of the cells to the microcarriers being impaired as little as possible.

In order to achieve a high coverage of the microcarriers in culturing, in particular, keratinocytes, it is further preferred to carry out the culturing first, in a first culturing phase, in an amount of culture medium as low as possible. This amount must be just high enough to ensure that the cells do not die to a considerable extent and are capable, at the same time, of binding to the surface of the microcarriers. It is only after the keratinocytes are adherently attached to the microcarriers to a considerable extent (usually after 6 to 8 hours) that, in a second culturing phase, further medium is added. The total amount of medium corresponds to that amount of medium which is optimally applied for the coverage of the microcarriers using uncritically growing epithelial cells, such as fibroblasts. For microcarriers which are known as carriers for adherent cells, this amount is usually specified by the manufacturer. In this context, the optimum amount of medium is 100 ml for 300 mg of Cytodex® (crosslinked dextran (matrix) and for 100 mg of Cultispher® (macroporous gelatin microcarrier). For culturing the keratinocytes, in the first culturing stage, only about 40 to 60% of this optimum volume of cell culture medium is added.

The examples and publications provided below shall illustrate the invention further, the protective scope of which is established by the patent claims. The methods described are to be understood as examples which describe the subject matter of the invention, even after modifications have been made.

EXAMPLE 1

Isolation and cultivation of human keratinocytes

1) Epidermal keratinocytes

Epidermal cells (keratinocytes) are isolated enzymatically from pieces of skin and foreskin, respectively, and are placed in the cell culture.

Isolation is carried out according to methods known in the art [Rheinwald, J. G., and Green, H., Cell 6 (1975) 331–334 (9); Limat, A., et al., J. Invest. Dermatol. 92 (1989) 758–762 (10); Rheinwald, J. G., Methods Cell. Biol. 21A (1980) 229–254 (12)].

The cultivation and proliferation of the keratinocytes until use for coverage of the microcarriers (MCs) is carried out in a static culture (cell culture flasks or cell factories) with serum-free medium.

2) Cells of the outer root sheath (ORS keratinocytes) from hair follicles

The establishment of primary cultures of ORS cells and expansion (cultivation) thereof in vitro is accomplished according to methods known in the art [Limat, A., et al., J. Invest. Dermatol. 92 (1989) 758–762 (10); Limat, A., and Noser, F., J. Invest. Dermatol. 87 (1986) 485–488 (13)].

EXAMPLE 2

Preparation of the microcarriers and cultivation of keratinocytes on microcarriers (MCs) (coverage of the MCs)

2.1 Preparation of the MCs for the cultivation a) Cytodex 3® (Pharmacia—crosslinked dextran matrix with a denatured collagen layer)

The MCs are weighed and allowed to swell in phosphate-buffered saline without calcium ions and magnesium ions (PBS -/-) overnight at room temperature (to be stirred up occasionally at the beginning). The PBS is decanted and the MCs are additionally washed twice with PBS; 50 to 100 ml PBS per gram of MC are applied.

The suspension is autoclaved (115° C., 15 psi, 15 min.) and thereafter the MCs are placed in culture medium (GIBCO, serum-free Keratinocyte-SFM). The MCs are washed once with culture medium and kept in the same medium at 4° C.

b) Cultispher® (Hyclone—macroporous gelatin microcarrier)

The MCs are weighed and allowed to swell in phosphate-buffered saline without calcium ions and magnesium ions (PBS -/-) overnight at room temperature (to be stirred up occasionally at the beginning). The PBS is decanted and the MCs are additionally washed twice with PBS; 50 to 100 ml PBS per gram of MC are applied.

Pre-coating with collagen

The suspension is autoclaved (115° C., 15 psi 15 min.). Subsequently, the MCs are stirred overnight at 37° C. in a solution of collagen S type 1 (3 mg collagen in 10 ml of 0.1% $CH_3COOH$); 10 ml collagen solution per 100 mg MC are applied. The supernatant is discarded, the MCs are washed once with PBS-/- and placed in culture medium (GIBCO, serum-free keratinocyte-SFM). After single washing (with culture medium), the MCs are kept in culture medium at 4° C.

2.2 Cultivation of the keratinocytes on the MCs

Subconfluent (about 70%) serum-free cultured keratinocytes (in cell culture flasks) of the first or the second passage are released from the bottom of the culture vessel using a trypsin/EDTA solution (5 ml per cell culture flask [175 $cm^2$ culture area] of a 0.05% trypsin/0.02% EDTA solution in PBS-/-, period of action: about 5 min. at 37° C). The release through trypsinization is stopped with 3 ml FCS (fetal calf serum). This suspension of individual cells is removed by centrifugation (10 min., at 180 g). The cell pellet is thoroughly resuspended in culture medium and cell counting is carried out using trypan blue.

Seeding with the MCs is carried out in a spinner flask (effective volume 50 ml). To about $1\times10^7$ cells are added 300 mg Cytodex 3-MC and 100 mg Cultispher respectively (about 10 cells per carrier) and the liquid volume is adjusted to 30 ml with serum-free culture medium.

Stirring in the spinner flask is carried out intermittently: 2 min. at 40 rpm, followed by 30 minutes of cultivation without stirring. These stirring conditions are maintained during the whole period of cultivation.

After 6 to 8 hours, medium is added until a volume of 100 ml is attained (possibly, the culture is transferred to a spinner flask having an effective volume of 250 ml). During the further period of cultivation, the medium is changed twice a day (about every 12 hours) according to the following procedure: The carriers settle on the bottom of the flask, spent medium is sucked off to the highest possible extent and replaced by fresh medium.

During the period of cultivation, the coverage of the MCs is evaluated microscopically and documented photographically. In the case of the Cytodex 3 MCs, the cells are evaluated without staining. In the case of the Cultispher MCs, the keratinocytes are stained with the Hoechst dye 33342 (2'-[4-Ethoxyphenyl]-5-[4-1-piperazinyl]-2,5'-bi-1H-benzimidazole) beforehand. Examples using cells on Cytodex 3 MCs:

FIG. 1: About 30% coverage.
FIG. 2: About 80% coverage.

After the desired coverage has been attained, excess medium (after the settling of the carriers) is sucked off and the remaining suspension is removed by centrifugation at 10 to 50 g for 10 min. A galenic substance is admixed to the pellet and the whole thing is applied in this form, or the pellet is frozen with the addition of a cryoprotectant for use at a later date. The table given below shows the extent of keratinocyte coverage of the microcarriers in dependence upon the optimizing process features:

intermittent stirring
increasing the volume of the medium after 6 to 8 hours

| Volume | Stirring | Coverage |
|---|---|---|
| constant | continuously | 0 |
| constant | intermittently | ~20% |
| increase 50% | continuously | ~20% |
| increase 50% | intermittently | ~80% |

It can be seen from Table 1 that each of these optimizing features contributes to enhancing the coverage. The combination of intermittent stirring and increase in volume leads to a decisive improvement of the coverage.

2.3 Fast cultivation of keratinocytes (Kz) on MCs

The MCs are incubated at a concentration of $1.2\times10^5$ MC/ml of culture medium with keratinocytes (cultured serum-free or with serum) at a concentration of $1\times10^6$ Kz/ml of culture medium. The ratio of MC:Kz is at least 1:10. The incubation takes place in a 13 ml centrifuge tube in an incubation cabinet (37° C., 5% $CO_2$, 95% rH) for at least 2 hours, not more than 6 hours, preferably for 3 hours. The suspension is to be shaken carefully once an hour for about 20 seconds. After that period, the majority of the Kz have adhered to the MC.

After 3 to 4 hours an aliquot is taken from the suspension and the coverage is examined microscopically.

| MC | Number of covered MCs, in % | Coverage density of the individual MCs, in % |
|---|---|---|
| Cytodex 3 | 50–70 | 70–90 |
| Cellgen | 70–90 | 70–90 |
| Biosilon | 50–70 | 40–70 |
| Cultispher | 0–5 | 0–5 |
| Collasphere | 0–5 | 0–5 |

EXAMPLE 3

Galenic medium

Keratinocytes alone (without beads) were mixed with several substances (but always with medium) and examined for viability. The results are as follows:

in gelatin: low viability;
in a number of ready-to-use wound gels/ointments: low or poor viability
in Nifucin-Gel® of the firm of Apogepha (nitrofurazone and adjuvant): good viability.

EXAMPLE 4

Determination of the coverage of the microcarriers:

The coverage of the microcarriers (determining the number of cells) is determined by means of protein determination. The protein determination is carried out according to the BCA method (test kit of the firm of Pierce, Catalogue No.: 23225).

Preparing the samples:

1 ml of a homogeneous suspension (microcarriers covered with cells in medium) is transferred to an Eppendorf vessel and removed by centrifugation in the Eppendorf centrifuge (2 min. at 10,000 rpm). The supernatant is discarded. The pellet is resuspended in 200 µl CAT lysis buffer (containing MOPS, NaCl and Triton X-100, pH 6.5, product of the firm of Boehringer Mannheim GmbH from CAT-ELISA-Kit, Catalogue No.: 1363727), resuspended and incubated at room temperature for 1 h.

Preparing the standards (standard series):

Keratinocytes from a confluent static culture are brought into suspension using a trypsin EDTA solution (0.05% trypsin/0.02% EDTA in PBS (Ca/MG-free). After the cell count (trypan blue method), 5 samples comprising in each case $1\times10^5$, $2.5\times10^5$, $5\times10^5$, $1\times10^6$, $2\times10^6$ cells are prepared from this cell suspension. The samples are removed by centrifugation (Eppendorf centrifuge, 2 min. at 10,000 rpm) and the pellets are resuspended in each case in 200 μl CAT lysis buffer (see above) and incubated at room temperature for 1 h. Subsequently, the protein determination of the standards and the samples is carried out according to the BCA method (see above). The OD values of the standards (x axis) are plotted in a diagram against the cell counts in the standards (y axis). The OD values of the samples are read with the help of this standard curve in cell count/ml.

Calculating the extent of coverage:
a) According to theoretical calculations, the microcarriers, at a coverage of 100%, carry, on an average, 40 keratinocytes/microcarrier.
b) The number of microcarriers employed in the samples is known: $4\times10^4$ microcarriers/ml sample.
c) The maximum possible number of cells in the sample (at a 100% coverage of the microcarriers) is: $1.6\times10^6$ keratinocytes/ml sample
d) The cell count/ml in the samples read from the standard curve (protein determination) is compared with the maximum possible number of cells (see above: c) and, from this, the extent of coverage of the microcarriers with keratinocytes, in percent, is calculated.

EXAMPLE 5

In vivo assay

Figure 3:
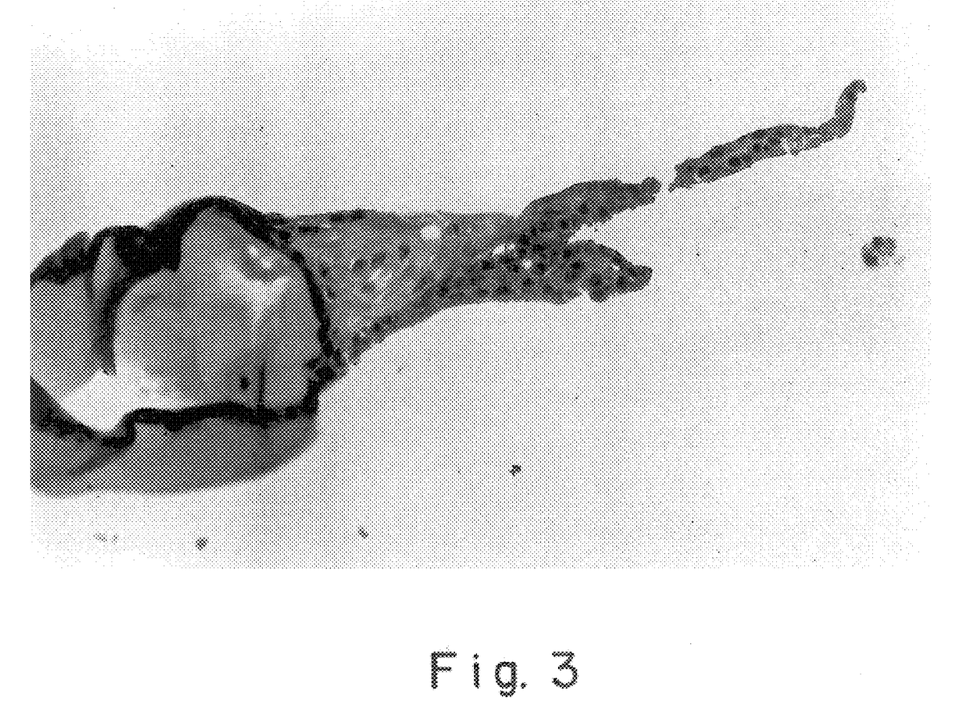
FIG. 3 shows the migration of keratinocytes on the artificial dermis (Example 5)

The migration of the keratinocytes from the MCs was examined on a slightly modified "Air-Liquid-Interface" model (Noser, F. K., and Limat, A., In Vitro Cell & Dev. Biol. 23 (8) (1987) 541–545 (34)). Collagen gels having inactivated fibroblasts embedded therein were used as the artificial dermis (Bell, E., et al., Proc. Natl. Acad. Sci. USA 76 (1979) 1274–1278 (35)). Into these gels in each case 200 ul of a MC keratinocyte suspension were seeded and cultivated, in a submersed manner, with a FCS-containing culture medium for a period of 24 to 48 hours. Subsequently, the gels were placed on a fine Teflon net and the same was disposed on a Teflon ring. This arrangement was placed in Petri dishes and cultivated for a period of up to three weeks. The serum-containing culture medium was exchanged completely every other day and the volume was measured such that it extended as far as to the lower edge of the Teflon net. For carrying out the histological or immunohistochemical examinations, the gels were lifted off from the Teflon net and were either fixed in a 4%-formalin solution and embedded in paraffin or subjected to cryoconservation. The histological sections of these preparations were dyed histologically with haematoxylin and eosin, or immunohistochemically with antibodies against CK-5, CK-10, mip (Ki67), and collagen IV. It was shown that migration of the keratinocytes takes place from the MCs onto the artificial dermis (FIG. 3), that the development of stratified dermis occurs, and that keratinocytes having basal properties are present in the preparation.

EXAMPLE 6

In vivo tests

Swine is the animal species suitable for the in vivo tests (Kangesu, T., et al., Br. J. Plastic Surgery 46 (1993) 401–409 (25); de Vries, H., et al., Wound Rep. Reg. 1 (1993) 244–252 (26); Breuing, K., et al., J. Surg. Res. 52 (1992) 50–58 (27)).
MC: microcarriers without any coating
MCG: carrier gel with 4% methyl cellulose (without any microcarriers)
Kzy+MC: microcarriers (beads) coated with keratinocytes The skin wounds are divided into five groups (group 1: control, without any applied substance; group 2: MC; group 3: MCG; group 4: MC+MCG; group 5: MC+MCG+Kzy). In order to be able to evaluate the tissue reactions occurring in each group, a number of seven preparations must be evaluated histologically. As the time course of the reaction is also important, the animals are examined after 3, 7 and 14 days. The points in time 3 and 7 days are covered by biopsies whilst after 14 days, the animals are sacrificed. Since as much as 30 skin wounds can be inflicted on each animal ((25), (26), (27)) there results a number of animals of n=5. On each animal 23 (3 times 7+2 reserves) skin wounds are inflicted.

Anesthesia:
Sedation with Ketamin/Azaperon im; initial anesthesia with Propofol iv; prolonged anesthesia: Isofluran, oxygen, nitrous oxide (intubation).

Operation:
Under absolutely sterile conditions, the skin areas are cleaned, freed from fat and disinfected, skin wounds of standardized sizes and depths are inflicted (with a pattern and a dermatome; size: 1.5×1.5 cm; depth: 3 mm), the substances to be tested are applied on the wounds, the individual wounds are covered by watertight and airtight vinyl chambers (these chambers allow separate observation of the individual wounds; such wound chambers are also used in clinics, for the covering of skin wounds; manufacturer: P.A. Medical Co., Columbia, USA).

Postoperative pain therapy:
As the skin wounds located on the backs of the animals, and the wound chambers placed thereon, cause pain and/or feelings of discomfort (e.g. itching) in the animals at least in the first postoperative phase, there is carried out routinely a therapy with Metamizol for a period of 3 days.

List of references
(1) Gallico, G. G., et al., New Engl. J. Med. 311 (1984) 448–451
(2) Cuono, C., et al., Lancet (1986) 1123–1124
(3) De Luca, M., et al., Burns 15 (5) (1989) 303–309
(4) Gallico, G. G., Clinics in Plastic Surgery 17 (3) (1990) 519–526
(5) De Luca, M., and Cancedda, R., Burns 18 (1) (1992) 5–9
(6) WO 92/06179
(7) EP-A 0 242 270
(8) WO 90/02796
(9) Rheinwald, J. G., and Green, H., Cell 6 (1975) 331–334
(10) Limat, A., et al., J. Invest. Dermatol. 92 (1989) 758–762
(11) DE 26 51 685
(12) Rheinwald, J. G., Methods Cell. Biol. 21A (1980) 229–254
(13) Limat, A., and Noser, F., J. Invest. Dermatol. 87 (1986) 485–488
(14) Brown, H., "Wound healing research through the ages", wound healing: biochemical and clinical aspects, Saunders, Philadelphia, page 5, editors: Cohen, I. K. Diegelman, R. F., and Lindblad, W. J., 1992
(15) Slivka, S. R., et al., J. Invest. Dermatol. 100 (1993) 40–46
(16) Regnier, M., et al., Skin Pharmacol. 3 (1990) 70–85
(17) Gboyse, S. T., et al., Plast. Reconst. Surg. 91 (1993) 632
(18) Burt, A. M., et al., Br. Med. J. 298 (1989) 915
(19) Hickerson, W. L., et al., Bums 2011 (1994) 52
(20) Keresztes, A., Kedvessy, G., Pharmacia 20 (1965) 371
(21) Sarkar, N., J. Appl. Polymer Sci. 24 (1979) 1073
(22) Sellerie, R., et al., Boll. chim. farmaceut. Milano 119 (1980) 41
(23) Daigo, K., et al., Yakuri to Chiryo 11 (1983) 401

(24) Langford, J. J., Dambach, A. E., Soap. Chem. Specialties 45/5 (1969) 231
(25) Kangesu, T., et al., Br. J. Plastic Surgery 46 (1993) 401–409
(26) de Vries, H., et al., Wound Rep. Reg. 1 (1993) 244–252
(27) Breuing, K., et al., J. Surg. Res. 52 (1992) 50–58
(28) Andreassi, L., et al., Wounds 3 (1991) 116–126
(29) Myers, S. R., et al., Abstract No. 85 in 5th Annual Meeting of the European Tissue Repair Society (August 1995), Padua
(30) Scharffetter-Kochanek, K., et al., J. Invest. Dermatol. 98 (1992) 3–11
(31) Lange, T. S., et al., J. Exp. Dermatol. 4 (1995) 130–137
(32) WO 92/09200
(33) WO 90/07577
(34) Noser, F. K., and Limat, A., In Vitro Cell & Dev. Biol. 23 (8) (1987) 541–545
(35) Bell, E., et al., Proc. Natl. Acad. Sci. USA 76 (1979) 1274–1278
(36) WO 91/17765

We claim:

1. A biomaterial suitable for the treatment of skin wounds, comprising keratinocytes attached to microcarriers, wherein said microcarriers exhibit an average coverage between 50 to 80% of the maximum coverage possible with keratinocytes.

2. The biomaterial according to claim 1, wherein said keratinocytes, are selected from the group consisting of autologous cells, allogenic cells and a combination of autologous cells and allogenic cells.

3. The biomaterial according to claim 1, wherein said keratinocytes are a combination of 10–30% autologous cells and 70–90% allogenic cells.

4. The biomaterial according to claim 1, wherein said microcarriers are biocompatible materials.

5. The biomaterial according to claim 4, wherein said biocompatible materials are selected from the group consisting of collagen, dextran, gelatin and silicon.

6. The biomaterial according to claim 1, wherein said microcarriers have diameter of 50 to 500 $\mu$m.

7. The biomaterial according to claim 1, wherein said microcarriers are pre-coated with a coating selected from the group consisting of eukaryotic cells or components thereof and extracellular matrix proteins, before said keratinocytes are attached.

8. The biomaterial according to claim 1, further comprising cryoprotective substances such that said biomaterial can be stored at a temperature between +3° C. to –196° C. prior to use.

9. The biomaterial according to claim 8, wherein said cryoprotective substances are selected from the group consisting of dimethyl sulfoxide and glycerol.

10. The biomaterial according to claims 1, wherein said keratinocytes are allogenic cells.

11. A method for preparing a biomaterial suitable for the treatment of skin wounds, comprising the steps of:
pre-culturing keratinocytes in a cell culture medium in the absence of microcarriers, then culturing the keratinocytes in the presence of microcarriers while intermittently stirring said keratinocytes, to produce keratinocyte covered microcarriers, and
isolating any keratinocyte covered microcarriers when said microcarriers are 50 to 80% covered with keratinocytes.

12. The method according to claim 11, wherein said keratinocytes are cultured in the presence of said microcarriers by stirring for 2 minutes at 40 rpm then culturing for 30 minutes without stirring.

13. The method according to claim 11, wherein said culturing of the keratinocytes in the presence of microcarriers is initially carried out in the smallest amount of cell culture medium required to prevent the keratinocytes from dying and after said keratinocytes are attached to said microcarriers additional cell culture medium is added to adjust the volume to a volume required for optimum growth.

14. The method according to claim 13, wherein said amount of cell culture medium is adjusted to the volume required for optimum growth after 6 to 8 hours.

15. The method according to claim 11, further comprising the addition of pituitary extract or fetal calf serum to said cell culture medium.

16. The method according to claim 11, further comprising forming a pharmaceutical formulation of said isolated keratinocyte-covered microcarriers, wherein said pharmaceutical formulation does not dehydrate said keratinocytes.

17. The method according to claim 16, wherein said pharmaceutical formulation comprises a hydrogel.

18. The method according to claim 17, wherein said hydrogel is selected from the group consisting of methyl cellulose, alginates, and agarose.

19. The method according to claim 11, further comprising precoating said microcarriers with a coating selected from the group consisting of epithelial cells or collagen before culturing said cells in the presence of said microcarriers.

20. The method according to claim 11, wherein said keratinocytes are cultured in serum free medium.

21. A method for treating a skin wound comprising the steps of:
applying a biomaterial comprising keratinocytes attached to microcarriers to said skin wound, wherein said microcarriers exhibit an average coverage between 50 to 80% of the maximum coverage possible with keratinocytes, and then covering said skin wound with a protective dressing.

22. The method according to claim 21, wherein said keratinocytes are selected from the group consisting of autologous cells, allogenic cells or a combination of autologous cells and allogenic cells.

23. The method according to claim 21, wherein said keratinocytes are a combination of 10–30% autologous cells and 70–90% allogenic cells.

24. The method according to claim 21, wherein said microcarriers, are biocompatible materials.

25. The method according to claim 21, wherein said microcarriers, have a diameter of 50 to 500 $\mu$m.

26. The method according to claim 25, wherein said microcarriers are pre-coated with a coating selected from the group consisting of eukaryotic cells or components thereof and extracellular matrix proteins, before said keratinocytes are attached.

27. The method according to claim 21, wherein said biomaterial is stored prior to use at a temperature between +3° C. to +10° C.

28. The method according to claim 21, further comprising the addition of cryoprotective substances such that said biomaterial can be stored at a temperature between +3° C. to –196° C. prior to use.

29. The method according to claim 28, wherein said cryoprotective substances are selected from the group consisting of dimethyl sulfoxide and glycerol.

30. The method according to claim 21, wherein said biomaterial is a mixture of stored and freshly prepared biomaterial.

31. The method according to claim 21, wherein said keratinocytes are allogenic cells.

32. The method according to claim 21, wherein said skin wound is selected from the group consisting of burn wounds, diabetic wounds, and senile ulcers.

33. The method according to claim 21, wherein said biocompatible materials are selected from the group consisting of collagen, dextran, gelatin and silicon.

34. A kit for treating a skin wound comprising a biomaterial containing keratinocytes attached to microcarriers, wherein said microcarriers exhibit an average coverage between 50 to 80% of the maximum coverage possible with keratinocytes, and a protective dressing selected from the group consisting of a fatty gauze dressing, a hydrophobic polymer dressing and a hydroactive dressing.

35. The kit according to claim 34, wherein said biomaterial and said protective dressing are in separate packages.

36. The kit according to claim 34, wherein said keratinocytes are allogenic cells.

* * * * *